United States Patent
Cisar et al.

(10) Patent No.: US 6,555,055 B1
(45) Date of Patent: Apr. 29, 2003

(54) SYSTEM FOR PREVENTING AND REMEDIATING BIOFILMS IN DENTAL EQUIPMENT

(75) Inventors: Alan J. Cisar, Cypress, TX (US); Adrain Denvir, College Station, TX (US); G. Duncan Hitchens, Bryan, TX (US); Thomas D. Rogers, Wheelock, TX (US)

(73) Assignee: Lynntech, Inc., College Station, TX (US)

(*) Notice: Subject to any disclaimer, the term of this patent is extended or adjusted under 35 U.S.C. 154(b) by 0 days.

(21) Appl. No.: 09/364,805

(22) Filed: Jul. 30, 1999

Related U.S. Application Data
(60) Provisional application No. 60/094,561, filed on Jul. 29, 1998.

(51) Int. Cl.[7] .............................. A61L 2/00; C03C 23/00; B01D 21/30; C25B 1/00; C25B 9/00
(52) U.S. Cl. .............................. 422/28; 422/22; 422/29; 422/62; 422/198; 422/292; 422/305; 134/2; 134/102.1; 134/22.1; 134/107; 134/36; 134/42; 210/136; 210/177; 210/205; 210/759; 210/764; 210/766; 205/343; 205/464; 205/628; 205/687; 205/701; 205/742; 204/266; 204/269; 204/270; 204/271; 204/274; 204/278
(58) Field of Search ................................ 422/3, 22, 28, 422/29, 38, 62, 198, 285, 305, 906; 134/36, 107, 102.1, 102.2, 2, 22.1, 211, 22.13, 22.17, 42; 210/759, 764, 177, 766, 136, 205, 206; 205/742, 466, 343, 464, 628, 687, 701, 633, 637; 204/274, 276, 269, 270, 271, 278, 266

(56) References Cited

U.S. PATENT DOCUMENTS

| | | | | |
|---|---|---|---|---|
| 4,198,296 A | * | 4/1980 | Doumas et al. ............... | 210/29 |
| 5,032,265 A | * | 7/1991 | Jha et al. ................. | 210/195.2 |
| 5,460,705 A | * | 10/1995 | Murphy et al. ............. | 204/252 |
| 5,645,700 A | | 7/1997 | White et al. ................ | 204/252 |
| 5,709,546 A | * | 1/1998 | Waggoner .................... | 433/82 |
| 5,762,779 A | * | 6/1998 | Shiramizu et al. .......... | 205/746 |
| 5,925,257 A | * | 7/1999 | Albelda et al. ............. | 210/748 |
| 5,972,196 A | * | 10/1999 | Murphy et al. ............. | 205/466 |
| 6,019,117 A | * | 2/2000 | Detsch et al. ................. | 137/15 |
| 6,019,905 A | * | 2/2000 | Waggoner ................... | 210/739 |
| 6,142,170 A | * | 11/2000 | Belfer et al. ................ | 137/240 |

* cited by examiner

Primary Examiner—Robert J. Warden, Sr.
Assistant Examiner—Monzer R. Chorbaji
(74) Attorney, Agent, or Firm—Streets & Steele; Jeffrey L. Streets (57) ABSTRACT

A system having a fluid source and a pasteurizer coupled with a disinfectant unit in flow communication with the fluid source for use in disinfecting dental or other water lines. The combination of pasteurizer and disinfectant unit is adapted to receive water from the fluid source. A fluid delivery unit is provided in flow communication with the pasteurizer and disinfectant unit combination. The disinfectant unit has a means for supplying hydrogen and oxygen and a means for generating hydrogen peroxide in flow communication with the means for supplying hydrogen and oxygen.

90 Claims, 6 Drawing Sheets

SYSTEM FOR PREVENTING AND REMEDIATING BIOFILMS IN DENTAL EQUIPMENT

This application is a continuation application claiming benefit of priority from the copending provisional patent application serial No. 60/094,561 filed on Jul. 29, 1998.

This invention was made with government support under contract number F41624-97-C-2004 awarded by the Air Force. The government has certain rights in this invention.

FIELD OF THE INVENTION

The present invention relates to the prevention and remediation of biofilms in dental equipment.

BACKGROUND OF THE INVENTION

Over the years the dental services community has become aware that the water systems currently designed for general dental practice do not deliver water of an optimal microbiological quality. It has been documented that dental unit waterlines harbor a wide variety of microorganisms including bacteria, fungi, and protozoans, which adhere to the interior surfaces of the waterline tubing to form colonies.

The American Dental Association (ADA) has recommended an ambitious and aggressive effort to encourage industry and independent researchers to improve the design of dental equipment by the year 2000 so that water delivered to patients during nonsurgical dental procedures contains no more than 200 colony forming units (cfu) of aerobic mesophilic heterotrophic bacteria per milliliter at any time in the unfiltered output of the dental unit (equivalent to an existing quality assurance standard for dialysate fluid in hemodyalisis units). This represents a massive decrease in microbial contamination of dental unit water from values that frequently run over 10,000 cfu/mL under current practice.

The organisms that currently contaminate dental units originate from a variety of sources, but the water lines of dental units represent the largest single source of biofilms. These biofilms live on the luminal walls of the water lines within the dental unit itself. The presence of adherent microbial biofilms in dental unit water lines was first reported more than 30 years ago. Interest in this issue has recently escalated throughout the world because many studies have confirmed the magnitude and widespread occurrence of contamination. In fact, one study found that the water coming out of dental unit water lines was of uniformly poorer quality than water coming out of taps in the same rooms.

The predominant organisms in dental water lines are Pseudomonas and Legionella species. Pseudomnonas are the most common organisms, but Legionella represent perhaps the most dangerous of the organisms routinely found in dental unit water lines (DUWLs). In one recent study, Legionella organisms were found in 29 out of 47 dental units tested. In many cases the organisms were present at a concentration of >$10^3$ per 10 mL sample.

The fact that aerosols generated from water within dental operatories are the source responsible for the elevated seropositivity to Legionella antibodies for dental personnel has been confirmed by several research studies. An Austrian serological study analyzing samples from 107 dentists, dental assistants and technicians found that thirty four percent (34%) tested positive to the polyvalent *L. pneumophila* antigen (the species considered most pathogenic to humans) comparing to only five percent (5%) from a non-medical workers control group. The highest prevalence (50%) was demonstrated among dentists, followed by assistants (38%) and technicians (20%). In an analogous study in the United States, 20% of the students and employees at a dental clinic in Virginia were seropositive for Legionella antibodies. Even though the higher seroprevalence rates have not been directly correlated with higher rates of disease among dental personnel, investigators speculate that it may reflect continuous exposure to small numbers of organisms resulting in mild (Pontiac fever) or inapparent infections.

Microbiologists have traditionally focused on free-floating bacteria growing in laboratory cultures. Recently they have realized that 99% of bacterial activity in open ecosystems occurs in biofilms adhered to surfaces. By 1990, researchers confirmed that biofilm bacteria are morphologically and metabolically distinct from free-floating ones, and that any bacterium can form a biofilm, once it finds a place to stick. As a result, biofilms, which were once considered odd curiosities, today are one of the hottest topics in microbiology since their occurrence has consequences for everything from medical technology to oil recovery.

Any solid surface immersed in an aquatic environment immediately serves as an adhesion site for macromolecules and other, low-molecular-weight hydrophobic molecules present in the water. This forms a so-called conditioning film which alters surface characteristics (such as hydrophobicity) and enhances the efficiency of subsequent bacterial adhesion.

The fundamental process of biofilm formation may be either passive or active. Some microorganisms already possess the necessary tools, such as extracellular polymeric substances or fimbriae and can immediately passively attach to a surface. Other bacteria require prolonged exposure to the surface to attach firmly. The active biofilm formation is a time-dependent process that begins with an initial reversible association between the microbe and the surface. During this period a genetic cascade is set off that turns on specific genes to make polysaccharides.

Due to the secretion of these substances and subsequent microbial multiplication, an irreversible adhesion and colonization of the surface is achieved. The production of a continuous fixed biofilm on the surface is then a function of cell division within the described polymeric matrix and can include the physical inclusion of other bacteria, fungi and protozoa from the free-floating microbial community of the surrounding water. All this eventually creates a slime layer composed of columns permeated by water-filled spaces through which materials and microbial by-products flow. The attached microbes have several survival advantages, in comparison to free-floating microorganisms.

Dental water lines, with their high surface-to-volume ratio, intermittent pattern of operation (with short periods of flow alternating with long, stagnant periods), and the characteristic of fluid dynamics in narrow, smooth-walled channels with only laminar flow, provide an ideal environment for microbial colonization.

The recognition of this health threat comes at the same time as an increasing awareness of potential occupational hazards in the dental office and concerns about increasing numbers of immunocompromised patients, such as elderly people, people with AIDS, cancer patients, diabetics, persons with chronic organic disorders or autoimmune diseases, and people who have received organ transplants or have recently received blood transfusions, all of whom have diminished resistance to opportunistic pathogens. All of these factors provide motivation for improving the quality of water for dental procedures.

Current methods for reducing water contamination are based on purging water lines for an extended period daily and a short period between patients or using independent water systems. The former method requires diligently following the procedure, and only reduces the bacterial count temporarily, and even then the reduction is not enough to meet the new standards. The latter method is only effective until the water system is contaminated once, and is then no better than using tap water.

Semiautomatic chemical treatments have been introduced that can be effective, but they require regular attention to keep the system filled with the disinfecting agent, and require an inventory of the agent be kept on hand at all times.

The current recommendations from the CDC for reducing the risk of contamination from dental unit water lines (DUWLs) involve a series of steps that must be followed conscientiously if they are to succeed. The first of these is the installation and use of anti-retraction valves (check valves to limit flow in a line to one direction) on all water and air lines. These devices prevent saliva and other fluids from the patient from being sucked back into water lines and colonizing the biofilm present in the water line. This is a concern because saliva from a patient's mouth is more likely to contain pathogenic organisms than the incoming water from a municipal water system. Accordingly, these valves must be regularly maintained to remain effective.

Pasteurization is widely used in the food industry, particularly for dairy products, but less often for drinking water, where chemical disinfection is usually preferred. Water pasteurization has received attention in recent years in two arenas. Solar heated pasteurization is generally viewed as a viable approach to improving the quality of drinking water in undeveloped areas. Pasteurization has been adapted by Murikami, et. al., to eliminate microorganisms from water in an ultra-pure water system.

A variety of values have been cited in the published literature for the times and temperatures required to kill waterborne microbes. Andreatta et. al., designed their system to reach 65° C. for at least a few minutes. A Mexican study concluded that 68° C. was the preferred pasteurization temperature, but this difference is insignificant. Filtration, to remove multicellular organisms, combined with two hours at 70° C. were recommended for sterilizing natural sea water. Goldstein demonstrated that a two minute exposure to a temperature of 76° C. was sufficient to kill up to 99.8% of all microorganisms in contaminated well water. Since the time needed to kill most organisms declines exponentially with increasing temperature, a 20° C. increase in treatment temperature produces an approximately four-fold reduction in time, and a 30° C. increase in temperature produces an approximately eight-fold reduction in time. In related work, Charm used a temperature of 75° C. for 0.05 seconds to kill viruses in blood.

The effectiveness of hydrogen peroxide as a general-purpose disinfectant is well recognized and its antibacterial effects have been studied and reviewed by a number of authors in recent years. Hydrogen peroxide can be synthesized electrochemically by the reduction of oxygen at the cathode of an electrochemical cell. The reduction of oxygen in both acidic and basic media has been extensively reported in the literature. In basic media oxygen reduction occurs either in a single four electron reduction to produce hydroxyl ions (shown in equation 1), $$O_2 + 2H_2O + 4e^- \rightarrow 4OH^- \qquad \text{Eq. 1}$$

or in two discrete steps, (equations 2 and 3), $$O_2 + 2H_2O + 2e^- \rightarrow H_2O_2 + 2OH^- \qquad \text{Eq. 2}$$

$$H_2O_2 + 2e^- \rightarrow 2OH^- \qquad \text{Eq. 3}$$

where the hydrogen peroxide is a stable reaction product, which can be utilized if it is promptly removed from the vicinity of the electrode to prevent further reduction. The mechanism of the reaction depends strongly on the type of cathode. Hydrogen peroxide is believed to be formed on iron during the rusting process. Carbon is reported to catalyze the hydrogen peroxide reaction in alkaline media while catalytic materials such as cobalt tetrakis(4-methoxyphenyl) porphyrin (CoTMPP) have been used to produce hydrogen peroxide under acidic conditions. Yields of 40% have been achieved with some carbon-supported porphyrin complexes.

Hydrogen peroxide, generated at the point of use, has already been demonstrated to offer particular advantages to the paper and pulp industries as a bleaching agent used to replace chlorine. The electrochemical method of production is cost effective for small scale operations. In the synthesis of hydrogen peroxide it has been suggested that a high surface area cathode is required for successful synthesis and the electrolyte must be free of any transition metal impurities as these catalyze the decomposition reaction to water.

The electrochemical reaction for the generation of hydrogen peroxide using a half fuel cell approach, based on proton exchange membrane (PEM) fuel cell technology is shown in Equations 4–6. On the anode side, humidified hydrogen gas is supplied to a porous electrocatalyst that breaks the hydrogen down to protons and electrons by the following reaction:

$$H_2 \rightarrow 2H^+ + 2e^- \qquad \text{Eq. 4}$$

The hydrated protons diffuse through the membrane electroosmotically until they reach the cathode. The cathode material is an electrocatalyst to catalyze the two electron reduction of oxygen to peroxide, as shown in equation 5, which is formed as a surface species on the catalyst. During the cathodic reaction $$O_2 + 2e^- \rightarrow O_2^- \qquad \text{Eq. 5}$$

the protons traversing the membrane react with the reduced oxygen species to form hydrogen peroxide, as shown in equation 6:

$$O_2^- + 2H^+ \rightarrow H_2O_2 \qquad \text{Eq. 6}$$

The hydrogen peroxide is then transported from the cell by the water present in the cell.

Thomas et. al., report that a concentration of at least 0.1% $H_2O_2$ is required for broad bactericidal action over a short time span (minutes), with higher concentrations (on the order of 1 to 3%) being effective in seconds, and substantially lower concentrations (as low as 0.0007%) suppressing bacterial growth (bacteriostatic action). Juven and Pierson report a similar concentration for bacteriostatic activity, 0.0005%, with 0.0034% marking the onset of bactericidal activity and 3% being quite effective against a broad range of pathogens. Lever and Sutton report effective bactericidal action in less than an hour for concentrations of 0.05% to 0.10%, increasing concentrations reducing the time required. These levels were also useful against viruses. The lowest concentration of hydrogen peroxide described as effective as a germicide comes from commercial formulations for hard surface cleaning agents. According to 21 CFR Part 178.1010 (c) (39), a concentration of 72 ppm hydrogen peroxide is the minimum level for use in an acidic sanitizing solution for use on food utensils and food handling surfaces.

Under current FDA rules, aqueous solutions of hydrogen peroxide with hydrogen peroxide concentrations between 1.5 and 3.0% are generally recognized as safe and effective for use as wound cleansing and healing agents for use in the mouth, and may be sold as such "over the counter" without restriction.

There are a number of products currently on the market that fall under this FDA rule. For example, two over-the-counter products include Colgate Peroxyl® Hygienic Dental Rinse (containing 1.5% hydrogen peroxide) and Metadent® toothpaste.

Most isolated, or clean, water systems cannot be sterilized. With these systems the only protection the system has is the diligence of the practitioner in only using sterile water and in following the manufacturer's instructions for periodic disinfection.

Besides being overly reliant on the diligence of the practitioner, current systems may also rely on an inventory of materials, such as a solution of hydrogen peroxide, to maintain their effectiveness. A diligent practitioner can maintain an inventory of any chemicals required, and use them regularly, but if the chemicals degrade in storage, as hydrogen peroxide does, all of this effort is for naught. Using under strength reagents is worse than no treatment program at all, since the act of using the weak materials will give the practitioner a false sense of security that they would not have in the absence of a treatment program.

Consequently, there is a demonstrated need for a system to mitigate the effects of biofilms by preventing the formation of biofilms in clean dental unit water lines (DUWLs) and eliminating biofilms from existing DUWLs. It would be desirable if the system did not heavily rely upon diligence of a practitioner or require reagents to maintain water quality.

SUMMARY OF THE INVENTION

The present invention provides a system for the prevention and remediation of biofilms in water lines, such as dental unit water lines. The system requires only electricity and the water being used by the dental unit to operate. The system consists of a series of steps, or unit operations, which together prevent the initial formation of a biofilm by preventing the entrance of microbes into the system and eliminates existing biofilms by introducing a disinfecting agent, hydrogen peroxide, capable of killing the organisms in the biofilm into the water stream. Any organisms not eliminated in these steps and much of the remains of the dead organisms are removed from the water stream by a final filter before the water is delivered to the patient. The action of this system can substantially reduce the risk of infection from water borne pathogens for both patients and practitioners.

DETAILED DESCRIPTION OF THE PREFERRED EMBODIMENT

The present invention provides a water pasteurizer to kill as many of the organisms in the incoming water stream as possible coupled with an electrochemical hydrogen peroxide generator to supply hydrogen peroxide on demand to kill surviving organisms and to aid in the extermination of existing biofilms when the unit is installed on an existing dental unit.

One of the key advantages of this system over existing ones is that it requires less user attention. By minimizing the user involvement human error is minimized and by carrying out all of the steps required to process tap water to a microbiologically acceptable quality in a single unit the chances of error are further minimized. Eliminating the need for added reagents means that the user does not need to maintain an inventory. This reduces costs, eliminates the possibility of running out of a key material, and eliminates worries about spilling stored material.

Small deionization units and prefilter assemblies that may optionally be added to the system are commercially available from a variety of sources and are adequately effective. With a pore size of 35 µm, the optional prefilter will remove clumps of microbes, such as pieces of biofilm which have detached from the water distribution unit, and any of the random debris that is found in any water system. This filter will not remove all of the microbes in the water, nor will it remove microbial spores.

A regenerative pasteurizer is used to reduce microbial concentrations by six to seven orders of magnitude. Most municipal water systems have microbial contents of $10^4$ cfu/mL, or less, and isolated water supplies have even lower microbial loads. This means that a six order of magnitude reduction in microbial content would produce a hypothetical microbial content of 1 cfu/100 mL, or less.

A heat exchanger is used to make the pasteurizer regenerative and reduce the amount of energy required to operate the system by at least a factor of two, with no improvements in the heat exchanger. Heating a liter of water from 25° C. to 95° C. requires about 81 Wh of energy. With the use of a heat exchanger this drops to less than 40 Wh.

The inventors have demonstrated that electrochemical generation of hydrogen peroxide can be accomplished using only the water that is being treated as a feed stock. Hydrogen peroxide is known to be effective as a bactericide when used at concentrations in the percent range and as a potent bacteriostat when used in concentrations of less than 100 ppm.

A distinct advantage of hydrogen peroxide is its safety and acceptability. Hydrogen peroxide is already accepted by the FDA for use in the mouth at concentrations up to 3%. This is above the 2% level that has been demonstrated by the inventors to be effective against existing biofilms. 3% is intended to be used as a periodic clean-out, with the solution purged from the system before a patient is treated, however, if the solution was not purged, it would not pose a health hazard.

Preferably, an optional final filtering step may be added to serve as a final barrier between the water supply and the patient. It may also serve to remove the remains of bacteria killed in the system.

It is also preferred to use one way valves or check valves in at least two locations in the system. A conventional check valve can be used to isolate the system from its water source. A standard anti-retraction valve can be used as the last step in the water line before it reaches the dental tool being used. These items are existing technology and are available from many sources.

Figure 1:
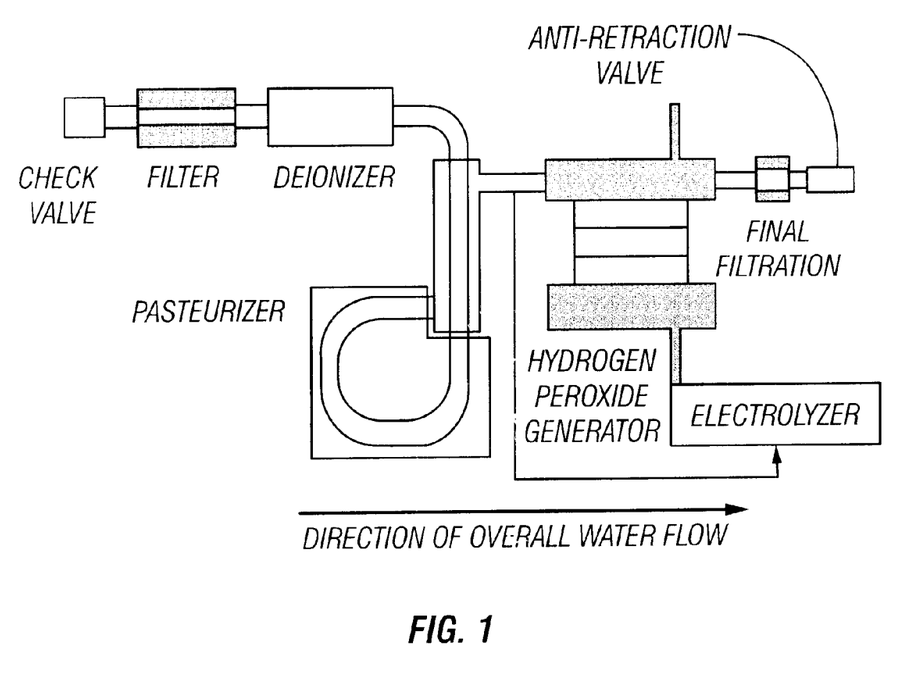
FIG. 1 is a schematic diagram of an exemplary system of hte present invention.
Figure 2:
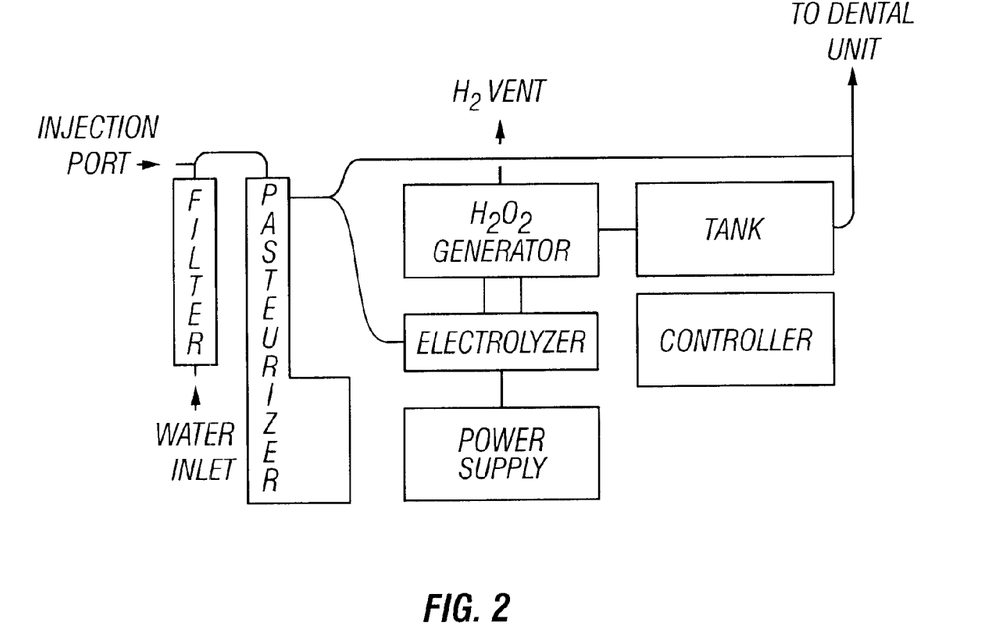
FIG. 2 is a schematic diagram of a system intended to supply hydrogen peroxide periodically.
Figure 3:
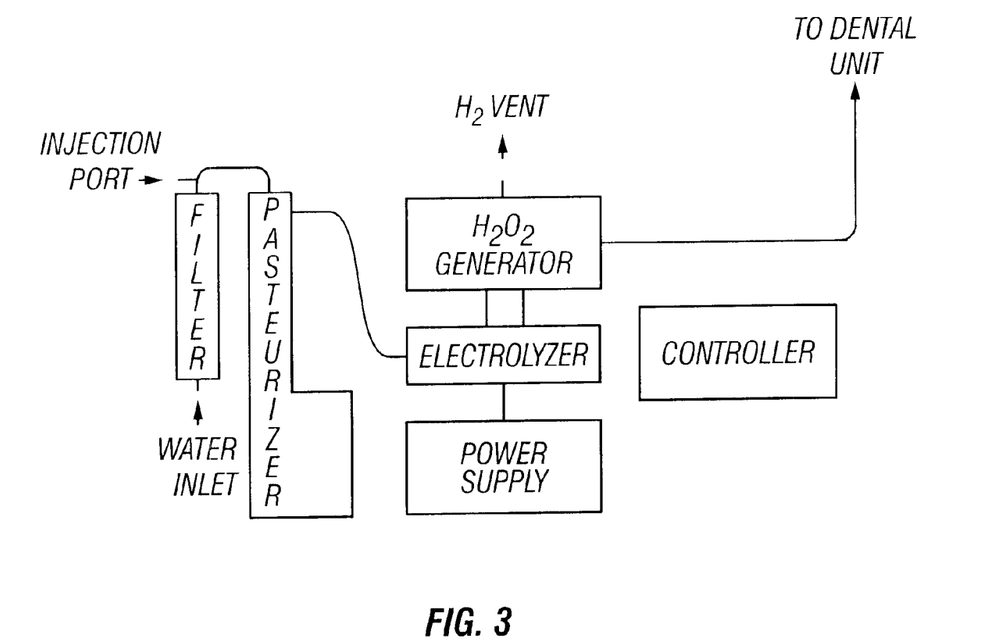
FIG. 3 is a schematic diagram of a system designed to deliver a constant bacteriostatic level of hydrogen peroxide.

FIGS. 2 and 3 show block drawings for two possible configurations of this system. FIG. 2 shows the configuration for a system intended to supply hydrogen peroxide periodically, i.e. once a day, to suppress and eventually eliminate a biofilm. FIG. 3 shows the configuration for a system designed to deliver a constant bacteriostatic level of hydrogen peroxide. Both functions could be combined in the same unit, if desired. A final filter, not shown, may be positioned at the base of the handpiece. This unit can be mounted on a dental unit, or can be set up as a stand-alone unit that delivers purified water to the dental unit.

In accordance with the present invention, the preferred temperature for pasteurization is 90° C., a temperature significantly above the normal pasteurization temperature of 60° C. The higher temperature is preferred to reduce the time needed to kill any given organism and increase the overall kill rate. (A two minute exposure to a temperature of 76° C. has been demonstrated to kill up to 99.8% of all microorganisms in contaminated well water.) Since the time needed to kill most organisms declines exponentially with increasing temperature, a 30° C. increase in treatment temperature produces an approximately eight-fold reduction in time.

The retention time of an aquidina tube is proportionate to length. Table I shows the length of tubes required for a one minute residence time at the flow rates needed for three primary water consuming dental operations or procedures. The numbers given in the headings represent outer diameters of the tubes. The inner diameters used to calculate the internal volume of the tubes were the standard diameters for stainless steel tubing (for example, a 0.25" tube has a 0.19" bore).

TABLE I

Length for Thermal Disinfection

| Use | Flow | | Length for 1 Minute Residence Time | | | | |
|---|---|---|---|---|---|---|---|
| | mL/sec. | mL/min. | 1/16" (m) | 1/8" (m) | 1/4" (m) | 3/8" (m) | 1/2" (m) |
| High Speed Handpiece | 0.6 | 36 | 28.4 | 8.77 | 1.97 | 0.91 | 0.42 |
| Syringe | 1.3 | 78 | 61.6 | 19.0 | 4.26 | 1.96 | 0.92 |
| Cuspidor Cup Fill | 19 | 125[a] | 98.7 | 30.5 | 6.83 | 3.15 | 1.47 |

It is clear from these numbers that, as expected, larger diameter tubes will require a shorter loop. If length was the only consideration, ½", or larger, diameter tubing would be the optimum choice. Another consideration is internal surface area. It is important that the water be heated effectively, and increasing surface area improves heat transfer. The internal surface for a tube sized to contain a constant volume of water increases linearly with the reciprocal of the diameter, i.e. a ¼" diameter tube has twice the internal surface of a ½" diameter tube, as illustrated in Table II. If surface area was the only consideration, 1/16" tubing, with the highest surface area, would be the best choice. Still another consideration is pressure drop, which increases rapidly as the diameter of the tube decreases. Table II shows the pressure drop for water flowing at a constant rate of 125 mL/min through tubes of several diameters. The pressure drop is shown for a tube one meter long and for a tube of the length required to hold a volume of 125 mL (taken from Table I).

TABLE II

Pressure Drop for Water at 125 mL per Minute

| External Diameter (in.) | Pressure Drop | | | |
|---|---|---|---|---|
| | Pa/m | psi/m | Pa(total) | psi(total) |
| 0.0625 | 14,726 | 1.02 | 1,453,143 | 100.2 |
| 0.125 | 877 | 0.060 | 26,699 | 1.84 |
| 0.250 | 24.3 | 0.0017 | 165.8 | 0.0114 |
| 0.375 | 3.77 | 0.00026 | 11.87 | 0.00082 |
| 0.500 | 0.605 | $4.17 \cdot 10^{-5}$ | 0.888 | $6.12 \cdot 10^{-5}$ |

With all of these factors considered, ¼" external diameter tubing is preferred. It offers a negligible pressure drop, it has double the surface area of the ½" tube, and the length required for each minute of residence time in the coil is not excessive. If the disinfection loop is arranged in a double coil, the coil will only occupy a volume of about ¾ L, arranged in a cylinder 3 in. high and 4 in. in diameter.

There are two primary advantages to equipping the pasteurizer with a heat exchanger. The first of these is to cool the water from the pasteurizing temperature in the pasteurizer to a more tolerable temperature for an individual's mouth, ideally about 35° C. The second is to reduce energy consumption required to heat the incoming water to the system. Not only does this reduce operating costs for the practitioner, but more importantly, it substantially reduces the amount of waste heat dissipated into the operating room.

The preferred heat exchanger for use in this system is a classic concentric counter flow shell-in-tube design. This type of heat exchanger is noted for being efficient and compact. In the experimental design for a typical dental office, the heat exchanger unit consisted of a 35 cm shell-in-tube heat exchanger with a 0.25" (6.35 mm) diameter inner tube fabricated from 304 stainless steel and an outer shell of 0.50" (12.7 mm) diameter, 316 stainless steel tube, with stainless steel fittings. The coil section was fabricated from an eight meter length of 0.25" diameter 304 stainless steel tubing arranged in a double layer helix.

The pasteurizer preferably includes three thermocouples: a first located at the exit from the inner, or tube, part of the heat exchanger; a second located inside the pasteurizer coil; and the third located at the exit from the outer, or shell, portion of the heat exchanger. These are used to monitor the performance of the heat exchanger.

Figure 4:
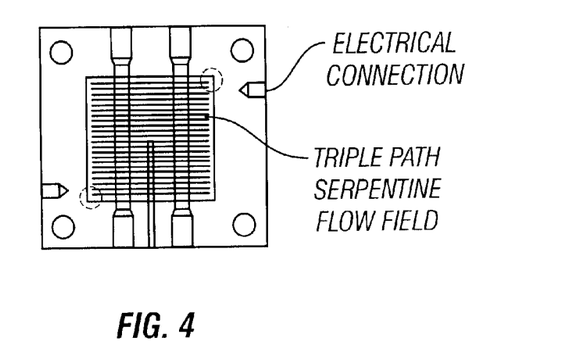
FIGS. 4 and 5 are schematic diagrams of front and back of an end plate for an exemplary electrochemical cell used in the generation of hydrogen peroxide.
Figure 5:
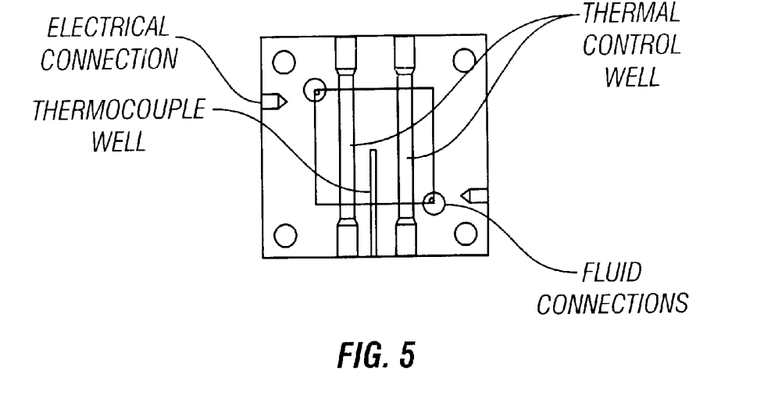

FIGS. 4 and 5 are schematic diagrams of front and back of an end plate for an electrochemical cell used in the generation of hydrogen peroxide. Each end plate was machined to allow the flow of the fluid electroactive species over the electrode. The active electrode area was 25 cm². Thermal wells allowed the temperature of the cell to be monitored and controlled and electrical connections allowed power to be supplied to the anodes and cathodes in a conventional manner. Before construction of the cell, the end plates were etched in hot phosphoric acid, rinsed in hot water then gold plated. The electrochemical cell may also take the form of a multi-cell stack.

Anytime that an active agent, such as hydrogen peroxide, is introduced into a system, there is a risk of a reaction or interaction between that agent and the materials of construction of the system. If hydrogen peroxide is to be introduced into a dental unit not designed with the use of hydrogen peroxide in mind, it is necessary to identify which materials are compatible with the hydrogen peroxide and which will be degraded by the peroxide. Consequently, several different materials were tested for compatibility with hydrogen peroxide. Ten and thirty percent hydrogen peroxide solutions were used in 48-hour exposure tests at a variety of temperatures ranging from 20° C. to nearly 100° C. Several materials were found to be suitable, such as ABS (Acrylonitrile-Butandiene-Styrene Terpolymer, CPVD (Chlorinated PVD), LDPE (Low Density Polyethylene), Polyphenylene Oxiden-Polyphenylene Ether (NORYL®), Polycarbonate, Polypropylene, PPS (RYTON®), PTFE (TEFLON®), PVD, PVDF (KYNAR®), EPDM (Ethylene-Propylene Copolymer) Polychlorotrifluoroethylene (KEL-F®), Natural Rubber, Silicone, TYGON®, Fluoroelastomer (VITON®), 304 Stainless Steel, 316 Stainless Steel, Aluminum, Bronze, Hastelloy-C, Titanium, Nylon, FLURAN®, Norton Performance, Plastics Corp., NORPRENE®, Norton Performance, Plastics Corp.

All dental units contain polymer tubing, but not all units contain o-rings or other gasket materials. Units such as those manufactured by Proma, use continuous tubes with pinch valves, virtually eliminating fittings.

The experimental determination of the hydrogen peroxide tolerance of seven types of o-ring materials was completed. Table IV contains a synopsis of the results. The abbreviations used in this table are defined in Table III. The columns are as follows: Polymer, the polymer being tested; ° C., the temperature at which the exposure took place; %H$_2$O$_2$, the concentration of the hydrogen peroxide solution used (0 indicates the water control in each group); saturated, indicates the observed weight gain after exposing the polymers to the solution and blotting the o-rings dry; and dried indicates the change in weight from the initial mass through saturation and drying as described in the experimental section.

TABLE III

Materials Used in Materials Compatibility Testing

| O-ring Materials | | Tubing Materials | |
|---|---|---|---|
| Material | Abbreviation | Material | Abbreviation |
| Ethylene-Propylene Co-polymer | EP | Clear Dental Unit Water Line Tubing (Polyethylene) | CDW |
| NEOPRENE ® (Chloroprene) | Neo | Red Dental Unit Water Line Tubing | RDW |
| Nitrile Rubber | Nit | Polyvinylchloride | PVC |
| VITON ® (Vinylidene Fluoride-Hexafluoropropylene) | Vit | Norprene Rubber | NOR |
| Silicone Rubber | Rsi | Latex Rubber | Lat |
| Aflas (TFE-Propylene) | Afl | Silicone Rubber | Rsi |
| TEFLON ® (PTFE) | TEF | | |

As indicated in Table VII, the seven polymer types fall clearly into four groups. The first group includes the three preferred polymers; VITON®, silicone rubber, and PTFE. The second group was acceptable and included Aflas. The third group was acceptable only at ambient temperatures and included ethylene-propylene copolymer. The last group including neoprene and nitrile rubber was found to be unacceptable.

TABLE IV

Experimental Determination of the Compatibility of Standard O-Ring Materials with Hydrogen Peroxide

| Polymer | ° C. | % H$_2$O$_2$ | Saturated | Dried |
|---|---|---|---|---|
| Recommended | | | | |
| VIT | 25 | 0 | 0.13% | 0.12% |
| | 25 | 1 | 0.34% | 0.11% |
| | 25 | 3 | 0.36% | 0.12% |
| | 25 | 10 | 0.14% | 0.17% |
| | 50 | 0 | 1.00% | 0.63% |
| | 50 | 1 | 0.84% | 0.56% |
| | 50 | 3 | 0.93% | 0.49% |
| | 50 | 10 | 0.90% | 0.39% |
| RSI | 25 | 0 | 0.36% | 0.03% |
| | 25 | 1 | 0.29% | 0.13% |
| | 25 | 3 | 0.31% | 0.06% |
| | 25 | 10 | 0.18% | -0.02% |
| | 50 | 0 | 0.31% | -0.05% |
| | 50 | 1 | 0.37% | -0.07% |
| | 50 | 3 | 0.30% | -0.02% |
| | 50 | 10 | 0.32% | -0.05% |
| TEF | 25 | 0 | 0.01% | 0.01% |
| | 25 | 1 | 0.02% | 0.08% |
| | 25 | 3 | 0.07% | 0.04% |
| | 25 | 10 | 0.02% | 0.04% |
| | 50 | 0 | 0.03% | 0.01% |
| | 50 | 1 | 0.01% | 0.00% |
| | 50 | 3 | -0.02% | 0.05% |
| | 50 | 10 | 0.06% | 0.02% |
| Acceptable | | | | |
| AFL | 25 | 0 | 0.56% | 0.31% |
| | 25 | 1 | 0.57% | 0.30% |
| | 25 | 3 | 0.57% | 0.88% |
| | 25 | 10 | 0.71% | 0.29% |
| | 50 | 0 | 1.00% | 0.53% |
| | 50 | 1 | 1.07% | -1.76% |
| | 50 | 3 | 1.71% | -3.19% |
| | 50 | 10 | 0.57% | -4.70% |
| Acceptable only at ambient temperature | | | | |
| EP | 25 | 0 | 0.93% | 0.54% |
| | 25 | 1 | 1.65% | 0.61% |
| | 25 | 3 | 2.56% | 0.81% |
| | 25 | 10 | 3.54% | 1.05% |
| | 50 | 0 | 2.65% | 2.00% |
| | 50 | 1 | 10.52% | 5.86% |
| | 50 | 3 | 27.70% | 15.80% |
| | 50 | 10 | 34.22% | 13.50% |
| Unacceptable | | | | |
| NEO | 25 | 0 | 2.00% | 1.37% |
| | 25 | 1 | 2.33% | 1.52% |
| | 25 | 3 | 2.13% | 1.45% |
| | 25 | 10 | 1.67% | 1.23% |
| | 50 | 0 | 11.15% | 8.54% |
| | 50 | 1 | 58.71% | 40.66% |
| | 50 | 3 | 108.38% | 62.01% |
| | 50 | 10 | 132.07% | 77.70% |
| NIT | 25 | 0 | 2.42% | 1.04% |
| | 25 | 1 | 3.66% | 1.42% |
| | 25 | 3 | 4.14% | 1.72% |
| | 25 | 10 | 4.53% | 2.34% |
| | 50 | 0 | 6.09% | 4.17% |
| | 50 | 1 | 19.17% | 12.30% |
| | 50 | 3 | 27.14% | 18.30% |
| | 50 | 10 | 63.26% | 45.08% |

The selection was made on the basis of the degree of swelling that occurred in the hydrogen peroxide solutions, and more importantly how much more the polymer swells in the hydrogen peroxide compared to how much it swells in water. The "recommended" polymers were virtually unaffected under any conditions. The "acceptable" polymer was unaffected at room temperature, but after drying showed evidence of weight loss in hydrogen peroxide at 50° C. The ethylene-propylene showed little damage at room temperature, but significant damage at 50° C. The "unacceptable" polymers showed serious to severe swelling and the drying cycle proved inadequate to remove all of the absorbed solution.

Table V shows the same data for the six water line materials as Table IV shows for the o-ring materials. The column headings are the same and are defined the same.

The selection was made on the basis of the degree of swelling that occurred in the hydrogen peroxide solutions, and more importantly how much more the polymer swells in the hydrogen peroxide compared to how much it swells in water. The "recommended" polymers were either virtually unaffected under any conditions or were generally less effected than the most commonly used dental water line tubing (polyethylene, labeled CDW) was in water. The "unacceptable" polymer, latex, showed severe swelling and degradation and the drying cycle proved inadequate to remove all of the absorbed solution.

Additional data was gleaned from the observations made during the course of the experiment. Each of the samples were visually examined daily without opening the vial. When the solution was changed in each of the vials on day four, the polymers were examined closely for deformations or other properties which might have changed. When the samples were kept at room temperature, there was no change to the polymers which were in the water, except RDW, which had some color loss in all solutions.

TABLE V

Experimental Determination of the Compatibility of Standard Dental Water Line Tubing Materials to Hydrogen Peroxide

| Polymer | ° C. | % H$_2$O$_2$ | Saturated | Dried |
|---|---|---|---|---|
| Recommended | | | | |
| CDW | 25 | 0 | 1.67% | 0.30% |
| | 25 | 1 | 1.32% | 0.97% |
| | 25 | 3 | 1.57% | 1.12% |
| | 25 | 10 | 5.20% | 1.45% |
| | 50 | 0 | 2.77% | 0.30% |
| | 50 | 1 | 11.20% | 1.01% |
| | 50 | 3 | 2.67% | 0.39% |
| | 50 | 10 | 2.05% | 0.21% |
| RDW | 25 | 0 | 15.89% | 7.13% |
| | 25 | 1 | 2.07% | 0.39% |
| | 25 | 3 | 4.16% | 4.61% |
| | 25 | 10 | 3.44% | 1.83% |
| | 50 | 0 | 4.32% | 3.81% |
| | 50 | 1 | 3.01% | 0.23% |
| | 50 | 3 | 2.59% | 0.45% |
| | 50 | 10 | 2.72% | 0.22% |
| PVC | 25 | 0 | 0.23% | 0.07% |
| | 25 | 1 | 0.38% | 0.07% |
| | 25 | 3 | 0.29% | 0.07% |
| | 25 | 10 | 0.30% | 0.04% |
| | 50 | 0 | 0.62% | 0.25% |
| | 50 | 1 | 1.01% | 0.36% |
| | 50 | 3 | 0.83% | 0.32% |
| | 50 | 10 | 1.40% | 0.28% |
| NOR | 25 | 0 | 2.24% | 0.25% |
| | 25 | 1 | 6.29% | 2.29% |
| | 25 | 3 | 0.68% | 0.14% |
| | 25 | 10 | 1.23% | 0.45% |
| | 50 | 0 | 2.99% | 2.44% |
| | 50 | 1 | 6.99% | 4.89% |
| | 50 | 3 | 7.29% | 1.87% |
| | 50 | 10 | 5.09% | 1.07% |
| SIL | 25 | 0 | 0.25% | 0.00% |
| | 25 | 1 | 0.59% | 0.00% |
| | 25 | 3 | 0.38% | 0.06% |
| | 25 | 10 | 0.13% | 0.03% |
| | 50 | 0 | 0.33% | 0.07% |
| | 50 | 1 | 0.21% | 0.04% |
| | 50 | 3 | 0.39% | 0.00% |
| | 50 | 10 | 1.82% | 0.04% |
| Unacceptable | | | | |
| LAT | 25 | 0 | 4.58% | 1.97% |
| | 25 | 1 | 4.93% | 2.12% |
| | 25 | 3 | 4.51% | 2.15% |
| | 25 | 10 | 4.19% | 2.11% |
| | 50 | 0 | 15.42% | 10.85% |
| | 50 | 1 | 24.34% | 17.71% |
| | 50 | 3 | 29.05% | 20.70% |
| | 50 | 10 | 38.85% | 25.76% |

In the 10% hydrogen peroxide, which was kept at room temperature, NOR showed some swelling along with a loss in its color. When the polymers were kept in water at 50° C., the PVC began to swell and turn cloudy; the RDW had some color loss; the CDW turned from a white to a yellow color; and the NOR showed some swelling. In 1% and 3% hydrogen peroxide, RDW had a loss in color; LAT was also bleached; PVC became cloudy, AFL had turned the hydrogen peroxide solution yellow; and CDW yellowed. The 10% hydrogen peroxide had the same effect on the polymer as 1% and 3% hydrogen peroxide for LAT, CDW, RDW, and PVC. NEO was one of the most severely damaged polymers in the 10% hydrogen peroxide, where it exhibited severe deterioration.

On the final day of the experiment, the polymers were examined closely once more. The RDW polymer had lost its color and was the only one effected by all the solutions at room temperature, including pure water. The loss of color observed here was surprising, since this specific piece of tubing had already been subjected to 17 years of service in the dental unit. Four of the polymers exposed to water at 50° C. had obvious changes. The PVC turned cloudy; NIT had turned the water cloudy and looked a little dull in color; RDW had a loss in color; and LAT had a slight color loss. When the polymers with 1% hydrogen peroxide were examined, LAT had lost some color and was swollen; RDW lost most of its color; AFL had turned the solution yellow and lost the shinny appearance; the PVC had turned cloudy; and NEO had deteriorated, cracked and swollen. In the 3% hydrogen peroxide, NIT would not return to its original shape if stretched; the RDW lost most of its color; NEO was swollen, deteriorated, gummy and cracked. AFL also yellowed the solution; PVC became cloudy and soft; and LAT had turned pale white, swollen, and was gummy. The 10% hydrogen peroxide had the greatest effect on the polymers at 50° C., as expected. The polymer LAT was pale, swollen and gummy; the PVC turned cloudy and soft; and AFL turned the solution slightly yellow. The final polymers which were examined with 10% hydrogen peroxide at 50° C. were NIT, NEO, EP, and RDW. The RDW had almost completely lost its red color; NIT was degraded, swollen, and easily deformed if stretched; NEO had cracks, along with being swollen and gummy; and EP had cracks and shredded when stretched.

In order for the proposed system to be used routinely in general dentistry the practitioner needs a method to quickly ascertain whether or not the system is producing an adequate concentration of hydrogen peroxide without the use of complex instrumentation. This means that a simple test is required that can be carried out quickly in a dental office.

There are hydrogen peroxide test strips already available on the market, but they are only able to detect low concentrations which makes them unsuitable for this application. To fill this need a new color change detection method was developed based on the same chemistry described in this report for the laboratory quantitation of hydrogen peroxide. This test was prepared in the form of a test vial. To test an unknown solution for hydrogen peroxide, 1 mL of the solution is added to the vial and the mixture well shaken. If the hydrogen peroxide concentration in the solution is at or above the threshold level for the vial a visible color change is observed in the mixture.

Figure 6:
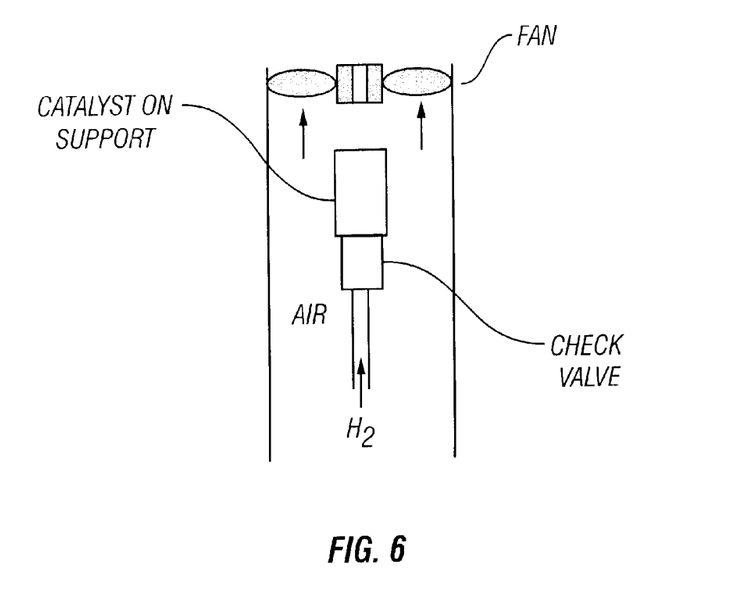
FIG. 6 is a schematic diagram of a system including a catalyzed substate for combustion of hydrogen.

One of the by-products of the electrochemical synthesis of hydrogen peroxide is hydrogen. The amount of hydrogen generated is small and the rate of generation is low. It could be safely vented but this may not be desirable. It is proposed to dispose of the hydrogen by purging it through a catalyzed substrate, similar to an automotive catalytic converter, where the hydrogen will be combusted (see FIG. 6). Hydrogen can be easily, flamelessly, and safely combusted on such a catalyst, even at temperatures as low as −10° C. The heat generated by this process will be slight, 0.1 to 0.6 Watts, and this can be easily dissipated with a simple cooling fan, in which case the fan will generate more waste heat than the hydrogen oxidation.

EXAMPLES

The following examples show the function of this invention and some of its preferred embodiments.

1. This Example Demonstrates the Effectiveness of Pasteurization for the Elimination of Microbes Form a Continuously Flowing Stream A Psuedomonas variety, *psuedonionas cepacia*, was selected as the challenge species for the pasteurization tests. The *Psuedomonas cepacia* was received from American Type Culture Collection (ATCC) in the form of a freeze-dried pellet. The bacteria was grown in a 15 mL test tube (Fisherbrand) with Difco Tryptic Soy Broth (TSB) for forty-eight hours at thirty degrees Celsius, to serve as a primary culture.

The challenge solution was "spiked" with a sufficient quantity of *P. cepacia* to yield a concentration of $5 \times 10^6$ cfu/mL in the plastic reservoir. (This concentration is three orders of magnitude more than the 2,000 cfu/mL found in the deionized water system in the laboratory, and actually leads to slightly cloudy water.) The pasteurization test apparatus was configured with a common pressurized feed tank connected to supply water simultaneously to two pasteurization units.

One of the pasteurizer units, the test unit, was heated to the test temperature, while the other unit was left at ambient temperature as a control. The feed container contained 10 liters of 0.85% sodium chloride which was then used to feed both pasteurizers. Flow rates were adjusted by controlling the pressure within the container. When the continuous, or constant, flow test was applied to the pasteurization system a sample was taken every ten minutes from both the cold and the hot pasteurizers with the flow rate changing every twenty minutes. In these tests, two samples were taken at each of the different flow rates used. Each of the tests started with roughly the same concentration of *Pseudomonas cepacia* suspended within the 15 liter reservoir which was attached to both pasteurizers. The concentration of cells in 0.85% sodium chloride solution was on average $5.0 \times 10^6$ cfu/mL.

Figure 7:
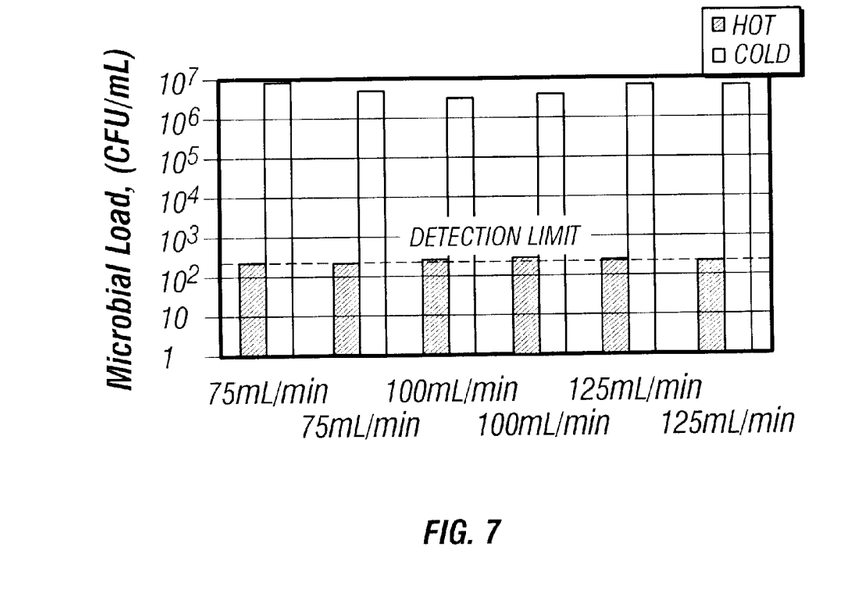
FIG. 7 is a graph of microbial load as a function of flow rate for both a hot and a cold pasteurizer.

The samples were serially diluted using 0.85% sodium chloride and plated on Tryptic Soy Agar (TSA) to yield a heterogenic plate count and colony forming units/mL (cfu/mL). This test did not allow for the heat exchanger to come to equilibrium with each change of flow rate. The flow rate was changed twice during the experiment with flow rates of 75 mL/min, 100 mL/min, and 125 mL/min used. As illustrated in FIG. 7, the test showed that the pasteurization system can reduce the concentration of bacteria within a water line by at least four orders of magnitude.

At a flow rate of 75 mL/min, the bacterial concentration in the solution was reduced to below the detection limit of 200 colony forming units (cfu/ml), for both of the samples which were taken. The results at a flow rate of 100 mL/min showed a four order of magnitude reduction but this did not quite reach the detection limit for each of the two samples. With the highest flow rate in this series, 125 mL/min, the reduction was still at least four orders of magnitude, but again not low enough to reach the detection limit for the first sample, although it was for the second sample. As shown in the graph, simply passing through an unheated pasteurizer (the control unit) has no effect on the organisms.

The concentration of cells found in the solution on the hot side was higher when the second sample was taken at 100 mL/min, because of the loss of heat that initially occurred when the flow rate was increased from 75 mL/min to 100 mL/min. The higher flow rate required more heat from the electrical heater, but because of the low heat conductivity of stainless steel, the heater thermocouple, located on the outside of the coil was slow to sense the falling temperature and increase the amount of power applied.

While operating at 75 mL/min, the pasteurizer coil had an internal temperature of 93–95° C. When the flow rate was increased, that temperature initially dropped to below 80° C. and gradually rose but was still below 90° C. when the second sample was taken. The detection limit was reached once again when the second sample was collected at 125 mL/min. By that time the heating rate had been increased sufficiently to bring the core temperature within the pasteurizer back to 90° C.

2. This Example Demonstrates the Effectiveness of Pasteurization for the Elimination of Microbes Under Conditions of Intermittent Flow A dental unit rarely, if ever, operates for an extended period under continuous flow conditions. Table VI shows the water flow rates required for the primary water consuming functions for a dental unit. All of these functions are intermittent, with flow only required for short intervals, after which flow stops for an extended period. The only one of these functions that is likely to require water for more than 15 or 20 seconds at a time is the high speed handpiece, and it requires the lowest flow rate. (It is these very features that make dental unit water lines such inviting places for the formation of biofilms.) The results of the test described in Example 1 exceeded the actual needs of a dental unit by a significant margin. Even with this stressful situation, the pasteurization system holds up to these conditions and proves that it can reduce the risk of infection to the practitioner and patients, under virtually any conditions.

TABLE VI

Water Consumption of Dental Instrumentation

| Use | mL/sec. | mL/min. |
|---|---|---|
| High Speed Handpiece | 0.6 | 36 |
| Syringe | 1.3 | 78 |
| Cuspidor Cup Fill | 19 | 125[a] |

[a]It is assumed that the cuspidor cup will be filled at most, once a minute.

Figure 8:
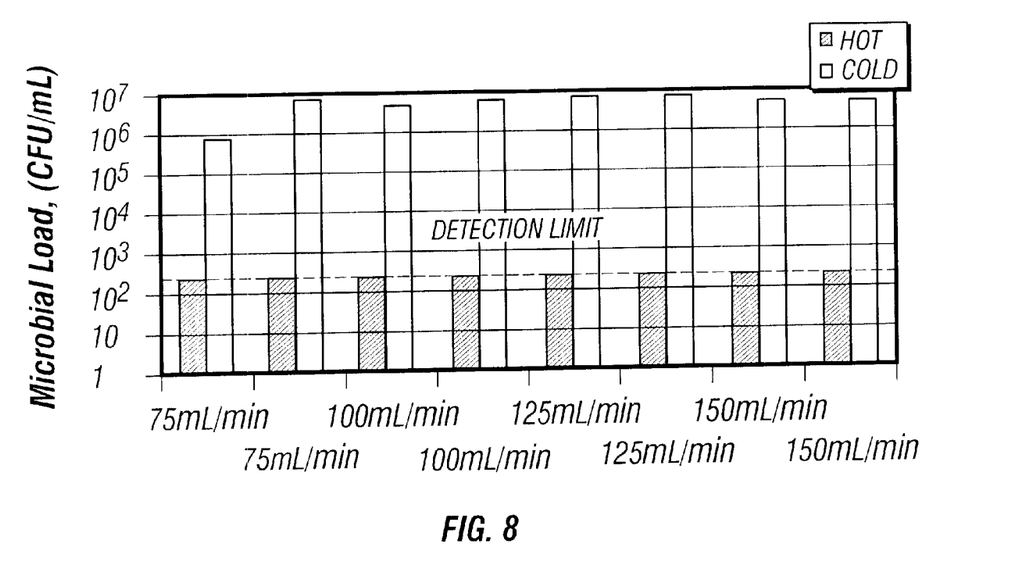
FIG. 8 is a graph of microbial load as a function of flow rate for both a hot and a cold pasteurizer.

A second test was performed using the same apparatus and reagents as were described in Example 1 with a non-continuous flow. This was carried out at four different flow rates, 75 mL/min, 100 mL/min, 125 mL/min, and 150 mL/min. The actual test was performed after allowing the unit to warm up for ten minutes. Each flow rate was run for two minutes, with the samples taken from both pasteurizers after one minute and after two minutes. At each of the designated flow rates, there were no organisms at the detection limit (200 cfu/mL) in any of the samples. As in the continuous flow experiments, the initial bacterial concentration in the reservoir was four orders of magnitude higher, and remained unaffected by passage through the unheated control pasteurizer. These results are shown in FIG. 8.

The control specimen had a slightly lower cell count in the first pair of samples. This is the result of settling when the reservoir was inadequately mixed at the start of the run. With a concentration of $5 \times 10^6$ cfu/mL the challenge solution is cloudy, and if allowed to stand, some of the organisms tend to settle out.

This test is considered to be a more accurate representation of the normal intermittent operation of a dental unit. Under these circumstances the temperature within the pasteurizer remained far more stable. The lowest temperature observed during this test was 77° C. after two minutes at a flow of 150 mL/min, far above ordinary operating conditions. Under these intermittent operating conditions the heat capacity of the pasteurizer was sufficient to compensate for the slow response of the heater. This points directly to a solution useful for a practical unit. That solution is the use of a thermal ballast, essentially a preheated heat sink, to supply heat and damp out temperature swings. This approach will permit the system to operate effectively using a simpler, and less expensive heater controller.

3. This Example Demonstrates the Electrochemical Generation of Hydrogen Peroxide The end plates illustrated in FIGS. 4 and 5 were used. The solid polymer electrolyte NAFION® 105 was prepared by boiling it in a solution of sulfuric acid for 60 minutes. This was followed by a washing procedure consisting of three cycles of boiling in deionized water with the water changed each cycle. The membrane was cut to the size of the endplates and the electrode materials were painted on. The anode was prepared by suspending platinum black (Fuel Cell Grade from Engelhard) in a NAFION® solution (Aldrich chemical Co., Milwaukee, Wis.). The solution was painted onto the membrane, then pressed for 1 minute at 150° C. with a force of 10,000 lbs.

The cathode material was prepared as follows. A weighed sample of cobalt (II) tetrakis-(4-methoxy)-porphine (CoTMPP) (Aldrich) was dissolved in methylene chloride. A weighed amount of high surface area carbon black (Vulcan-XC27R, Cabot) was dispersed in the solution. The methylene chloride was then evaporated in a rotary evaporator under vacuum at 80–90° C. to dryness. To bond the porphyrin onto the carbon the powder was pyrolized in an argon atmosphere at 700° C. for 1 hour. The pyrolized residue was weighed and added to another portion of methylene chloride solution that contained the complex CoTMPP to increase the porphyrin loading on the carbon substrate. This procedure was repeated until there was 10% loading of the catalyst on the carbon substrate. The powder was suspended in a Nafion/water mixture then painted onto the membrane and pressed for 1 minute at 150° C. with a load of 10,000 lbs.

Figure 9:
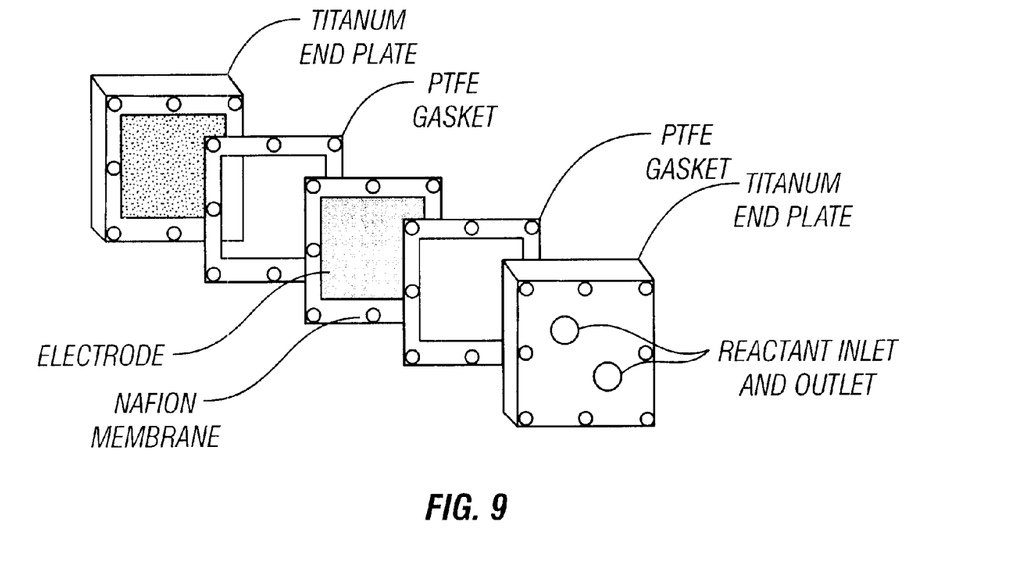
FIG. 9 is an exploded view showing the assembly of a cell.

The cell was assembled as shown in FIG. 9. The solid polymer electrolyte/electrode assembly was placed between the end plates and sealed in place with unsintered PTFE (GoreTex) gaskets that were cut to size. This gave a "Zero Gap" cell configuration. The end plates were then restrained together using four stainless steel bolts covered with electrical insulation to insure the electrical isolation of the two endplates.

To generate the hydrogen peroxide, a constant current was applied between the two electrodes using a Lambda LLS9040 power supply for precise current control. Humidified hydrogen and oxygen gases were fed into the anode and cathode compartments respectively at 40 psi. The hydrogen peroxide solution leaving the cathode chamber was collected in a pressure reactor. For experimental purposes, the hydrogen and oxygen gases were supplied from pressurized tanks to eliminate the need to couple the system directly to an electrolyzer. However, it would be preferred to supply gases from a directly coupled electrolyzer unit capable of producing both hydrogen and oxygen.

Upon completion of the electrolysis, the concentration of hydrogen peroxide was determined by titration. A quantitative aliquot of the hydrogen peroxide solution was taken and made up to 40 mL with DI water. Sulfuric acid (1 mL), and 2 drops of manganese sulfate solution (4 grams in 20 mLs of water) were added. The mixture was titrated with potassium permanganate solution until the first signs of violet appeared. The concentration of hydrogen peroxide in the solution was calculated from the titration results. The reaction is illustrated in equation 7:

$$2KMnO_4 + 5H_2O_2 + 3H_2SO_4 \rightarrow 2MnSO_4 + K_2SO_4 + 8H_2O + 5O_2 \uparrow \quad \text{(Eq. 7)}$$

In these experiments hydrogen peroxide was generated in a 25 cm² single cell stack with a Cobalt tetrakis(4-methoxyphenyl)porphyrin catalyst ink cathode. Humidified hydrogen gas was supplied to the anode compartment and humidified oxygen supplied to the cathode compartment, both at a pressure of 40 psi. A current of 5, 10, 15, or 20 Amps was applied between the two electrodes for 2 hours. The concentration of hydrogen peroxide in the catholyte stream was determined by titration with potassium permanganate as described in the experimental section. The results of the experiment are shown in Table VII.

TABLE VII

Electrochemical Synthesis of Hydrogen Peroxide.

| Applied Current (Amps) | Product Volume (mL) | $H_2O_2$ Concentration (%) | Current Efficiency (%) |
|---|---|---|---|
| 5 | 19.4 | 0.9 | 2.78 |
| 10 | 20.0 | 1.6 | 2.55 |
| 15 | 18.6 | 1.3 | 1.28 |
| 20 | 21.2 | 2.2 | 1.86 |

The table shows two trends that occur as the applied current increases. The concentration of peroxide in the exit stream increases with increasing applied current, while the current efficiency decreases.

This increase in concentration with increasing current is expected because the current is a direct measure of the amount of reaction occurring, thus a higher current results in more product. However the current efficiency of the reaction drops as the applied current increases. The current efficiency is a measure of how much of the applied current is being used in the desired reaction and is equivalent to selectivity for thermocatalytic reactions. Current efficiency is related to the amount of product formed in an electrochemical reaction by:

$$\text{cur. eff.} = \frac{\text{charge for desired reaction}}{\text{total charge passed}} \quad \text{(Eq. 8)}$$

The low current efficiencies observed here show that with this catalyst selectivity for hydrogen peroxide is low, with the formation of water being the dominant reaction.

The humidity of the gases was increased by increasing the temperature of the water in the spargers and the experiment was repeated at the 5 Amp current level for 2 hours at 40 psi. Analysis of the experiment showed that there was an increase in concentration from 0.9% to 1.0%. The volume of liquid collected in the experiment had also increased along with the current efficiency for the reaction, which increased from 2.78% to 3.50%.

The protons that are involved in the formation of hydrogen peroxide, as well as those forming water, are transported through the membrane in a hydration sphere of water molecules. Increasing the humidity may be producing increased water transport, leading to a more rapid removal of the product from the vicinity of the catalyst, before the hydrogen peroxide can be further reduced to water.

Hydrogen peroxide exhibits biostatic control at concentrations below of 0.1% and efficient biocidal control at concentrations of 1%. In these experiments it has been shown that hydrogen peroxide can be generated electrochemically in concentrations that are sufficiently high to exhibit biostatic or biocidal action.

Figure 10:
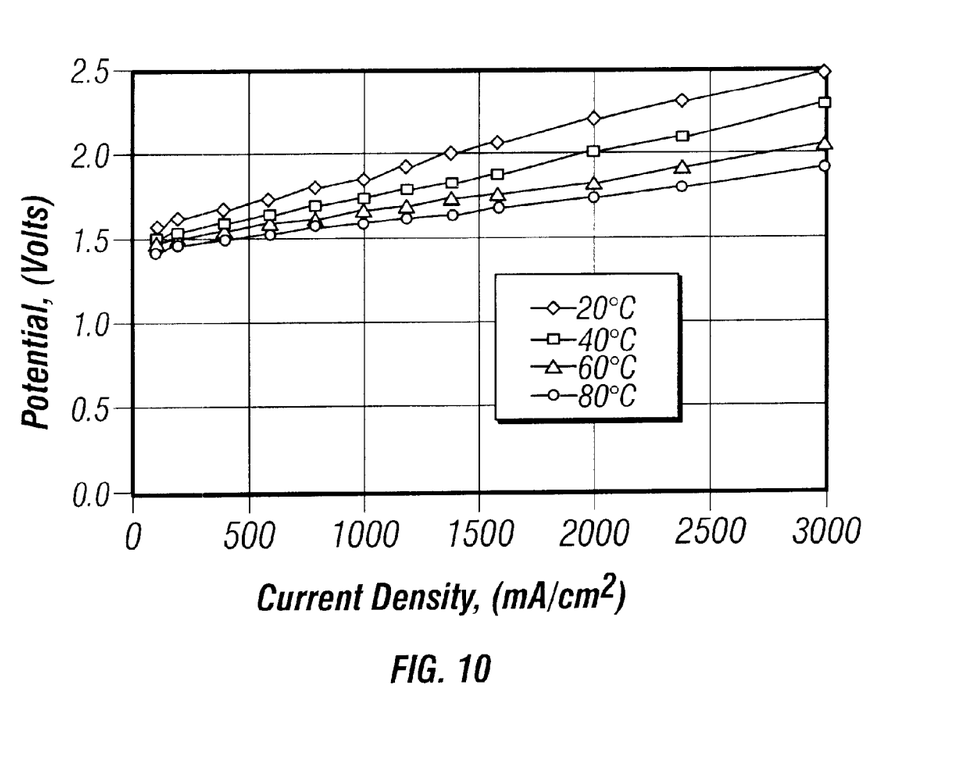
FIG. 10 is a graph of cell operating potentials measured at various current densities and operating temperatures.

3. This Example Demonstrates the Operation of the Electrolyzer Needed to Supply Hydrogen for Use in the Synthesis of Hydrogen Peroxide A single cell PEM electrolyzer was operated over a range of temperatures and current densities to demonstrate the unit's efficiency over the range of operating temperatures likely to be encountered by a unit operating in a dental office. The data obtained were plotted as shown in FIG. 10. The electrolyzer, when operated at a current density of 1,000 mA/cm$^2$ (a typical operating point for a PEM electrolyzer) requires a potential of 1.86 Volts at 20° C. This is a conversion efficiency of 65.6%, indicating that nearly two-thirds of the power put into the electrolyzer goes to the production of hydrogen, with the remainder going to waste heat. While operating, the unit will self-heat, and as the temperature goes up, the potential required declines until at 80° C. a potential of only 1.60 Volts per cell is required for a 76.3% conversion efficiency.

5. This Example Demonstrates the Impact of Hydrogen Peroxide on Biofilms

Due to the unique properties of the biofilm created by a variety of organisms, an established biofilm is quite difficult to destroy using chemical methods. The goal, however, of this project is to show that even an established biofilm can be controlled by the regular application of a hydrogen peroxide solution. An experiment was carried out to demonstrate that hydrogen peroxide was effective in remediating existing biofilms.

The apparatus used consisted of two air cylinders containing compressed breathing air, two NALGENE 5 L and 15 L bottles, and the dental unit. The experiment consisted of first re-invigorating an established biofilm in a previously used dental unit (A-Dec, a 1980 model) by running tap water, which had been determined to have a bacterial count of 10$^4$ cfu/mL, through the apparatus at hourly intervals between 9:00 a.m. and 4:00 p.m. for a total of 10 days. The water source was then switched from tap water to filter sterilized, deionized water for a period of three days, since this was the water to be used in the unit after the hydrogen peroxide treatments were started in order to remove the background of 10$^4$ cfu/mL that the tap water would produce even in a biofilm-free system. This limited the organisms monitored to those originating from the biofilm.

Only one bottle was used at a time, either one containing deionized water (filtered through a 0.2 micron filter), or one containing a 1% H$_2$O$_2$ solution (Kroger brand 3%, diluted with deionized water to a 1% solution). Every morning at 9:00 a.m., the H$_2$O$_2$ bottle was connected to the compressed air cylinder and the junction box (which connects the reservoir to the dental cart). The second air cylinder was directly connected to the junction box which provided air to the dental cart tools and allowed the peroxide or water solution to be misted out of the high-speed handpiece to simulate dental office use. Both air cylinders were opened, and H$_2$O$_2$ was run through the unit by pressurizing the bottle. A 50 mL bolus of the H$_2$O$_2$ solution was run through as the line to the dental cart/handpiece holds approximately 40 mL. The H$_2$O$_2$ bottle was then removed, and the bottle containing only water was connected into the set-up in exactly the same way. Approximately 150 mL of water were run through the unit to ensure that all of the H$_2$O$_2$ was rinsed out of the line. For the remainder of the day, to simulate normal operation in a dentist's office where the water is left stagnant 99% of the time, the line was flushed with 150 mL of water every hour. At 4:00 p.m., a 2 mL sample of water was collected from the high-speed handpiece into a 15 mL sterile centrifuge tube (Fisher brand). The sample taken after H$_2$O$_2$ treatment and the hourly flushings was diluted (using a sterile 0.85% NaCl solution) and 0.1 mL plated on pre-poured, sterile, Tryptic Soy Agar plates (International BioProducts, Inc.) to give a heterogenic plate count and determine the microbial load in cfu/mL. The plates were counted using a MANOSTAT brand colony counter after 2–3 days incubation time at 37° C., selected as the optimal growth temperature for human pathogens.

Once the biofilm had been refreshed, the unit was treated with a 1% H$_2$O$_2$ solution daily at 9:00 in the morning by running 50 mL of solution through the lines of the unit. After the H$_2$O$_2$ treatment, 150 mL of sterile, deionized water was run through the unit at hourly intervals between the hours of 9:00 a.m. and 4:00 p.m. to simulate normal dental office operating conditions, where water is left stagnant most of the time. On day 35, the unit was treated for 4 days with 2% H$_2$O$_2$ in the same manner previously described. This was done to assess the effect of higher concentrations of peroxide on the biofilm.

On day 40, the peroxide treatment procedure was changed slightly. Instead of applying the 2% H$_2$O$_2$ solution in the morning it remained in the dental lines overnight. From 9.00 a.m. to 4 p.m. daily the unit was flushed with 150 mL of sterile water. However, at 4.00 p.m., 50 mL. of 2% hydrogen peroxide solution was run through the unit and allowed to stay in the line overnight. At 9.00 a.m., the following morning, the sterile water flushes began again.

At the end of the day after the last flushing, a 2 mL sample of water was collected from the hand piece. This sample was then serially diluted using a 0.85% NaCl dilution media and 0.1 mL of the diluted solution plated onto Tryptic Soy Agar Plates. After incubation, a heterogenic plate count was made for each daily sample.

Figure 11:
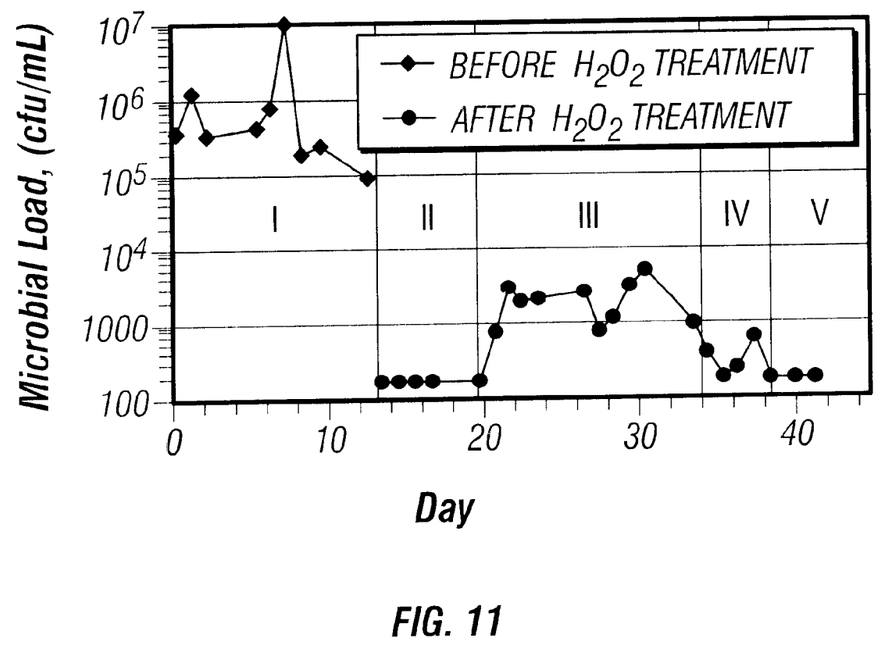
FIG. 11 is a graph of microbial load as a function of time, illustrating the impact of hydrogen peroxide on an existin biofilm.

The resulting data illustrating the impact of $H_2O_2$ on the existing biofilm can be seen in FIG. 11.

As Region I of the graph illustrates, the samples taken before any $H_2O_2$ treatment have quite high microbial concentrations (all $\geq 10^5$ cfu/mL), some reaching greater than $10^7$. For the first 10 days, this includes contamination from the tap water running through the system. At day 10, the water source for the unit is changed to a sterile water source. The sterile water going into the apparatus is contaminated when parts of the biofilm and cells adhering to the biofilm are shed into the flowing water and the count remains high.

Region II of the graph illustrates the effect that the initial applications of $H_2O_2$ had on cfu/mL. When $H_2O_2$ was applied in the morning, and a sample taken in the afternoon after hourly flushings, the cfu/mL were too few to detect (fewer than 200 cfu/mL). The $H_2O_2$ initially had a larger impact than in Region III because the biofilm system and individual cells from the system were shocked. The cells adhering to the biofilm that were shed into the water were not able to form colonies for several days. By day 21, however (illustrated by Region III), the biofilm system was able to come back and colonies once again began forming on the Tryptic Soy Agar plates, although with a 2 to 3 order of magnitude decrease compared with the untreated samples of Region I. This data strongly indicates that treatment of an existing biofilm with a 1% $H_2O_2$ solution once a day significantly decreases the number of colony forming bacteria that are released through the handpiece into the environment. A 2% solution of hydrogen peroxide results in lower bacterial cell counts than a 1% solution as shown in Region IV. From day 40 onwards, the dental water lines were left overnight in 2% $H_2O_2$ solution. The initial results from this method indicates that the bacterial count is negligible (fewer than 200 cfu/mL). These results suggest that soaking the water lines overnight in a hydrogen peroxide solution, causes a significant reduction of colony forming bacteria released in the water.

6. This Example Demonstrates a Convenient Test for Determining the Concentration of Hydrogen Peroxide in an Aqueous Solution The chemical reaction used to visually determine the concentration of hydrogen peroxide is the same one that is used to quantitatively determine the presence of hydrogen peroxide, as illustrated in Equation 7 in Example 3.

Test vials for determining hydrogen peroxide concentration were prepared as follows: Four milliliters of a 0.1 M potassium permanganate solution (Aldrich) was mixed with DI water (25 ml), sulfuric acid, 1.0 mL, (Fisher), and two drops of a manganese sulfate solution (0.4 g in 20 mL of water) in 40 mL glass vial. These quantities are correct to determine the presence of 1% hydrogen peroxide when 1 mL of the hydrogen peroxide solution is used for the test. The permanganate concentration can be easily adjusted to determine other concentrations in this simple test, and the entire test can be scaled to function with a smaller sample.

To test an unknown solution for hydrogen peroxide, 1 mL of the solution is added to the vial and the mixture well shaken. If the hydrogen peroxide concentration in the solution is at or above the threshold level for the vial a visible color change in the mixture is observed.

Potassium permanganate produces a purple colored solution, the starting reagent color. Three hydrogen peroxide solutions, having concentrations of 2%, 1%, and 0.1%, were prepared in DI water. A 1 mL aliquot of each was removed, added to a vial containing the test solution, and mixed thoroughly.

Bottle A received the 2% hydrogen peroxide solution and it was seen that the solution turned from purple to colorless. The bubbles visible near the top are oxygen, evolved during the reaction. Bottle B received the 1% hydrogen peroxide solution. The solution was partially bleached, yielding a cloudy brown color. The brown color is the result of an insoluble manganese compound that will precipitate on standing. Bottle C received the 0.1% hydrogen peroxide. No color change was observed.

Vials of this type can be prepared to cover a wide range of hydrogen peroxide concentrations and samples sizes. Both the starting reagents and the products of the reaction are safe for disposal in conventional municipal sewage systems, so at the completion of a test, the vial can be dumped in the sink, rinsed out, and the glass tossed in the trash.

7. This Example Demonstrates the Stability of the Test Solutions Used in Example 6

A vial of the color change test solution prepared in Example 6 was allowed to stand at room temperature (fluctuating between 21 and 25° C.) under fluorescent light for 30 days. At the end of this time, no change in color was apparent, indicating that this reagent is stable.

8. This Example Demonstrates the Effectiveness of Filtration for Reducing the Microbial Content of Water A point-of-use microfiltration system is preferably used as a polishing step to remove any remaining bacteria, live or dead, from water. The filter fits into the water lines directly behind the handpiece, meaning that each dental unit requires several filter units. These filters have a 0.45 $\mu$m pore size and are effective at preventing the passage of bacterial cells. The filter system is easy to install, but the filter must be changed regularly.

The equipment, a STERIFIL Aseptic System (Millipore), was used. Tap water was collected in sterile centrifuge tubes (FISHERBRAND) and a 1 mL aliquot was removed and plated using BioPro Tryptic Soy Agar (TSA) plates (International BioProducts Inc.) using the method previously described. The water was filtered through a Millipore type HA 0.45 $\mu$m filter then collected in the receiving flask where a 1 mL sample was removed and plated out.

The water was filtered through a Millipore type HA 0.45 $\mu$m pore size filter then collected in the receiving flask where a 1 mL sample was removed and plated out. The plates were allowed to incubate for 2 days at 37° C. in a Gravity Convection Incubator (Precision Scientific) before they were removed and the number of colonies counted. A typical set of results are illustrated in Table VIII.

TABLE VIII

Effect of Filtering on the Bacterial Content of Water

| Sample | Bacterial Content (cfu/mL) |
|---|---|
| Unfiltered tap water | $3.8 \times 10^4$ |
| Filtered tap water | <200 |

As indicated by these results, the 0.45 μm filter reduced the number of bacteria in the filtrate from $3.8 \times 10^4$ to an undetectable level. Using a filter of this type on the exiting water stream will effectively remove any organisms that have survived the other steps. It will also remove the remains of organisms killed in the system.

What is claimed is:

1. An apparatus for combating biofilms in a water line, comprising:
   a pasteurizer receiving the water line, the pasteurizer having a heater for heating the water flowing through the line;
   an electrochemical hydrogen peroxide generator having a cathode in fluid communication with the water line downstream of the pasteurizer, wherein the cathode produces hydrogen peroxide;
   an electrolyzer having an anode in fluid communication with the water line and the cathode of the hydrogen peroxide generator; and
   a fluid outlet in fluid communication with the water line downstream of the hydrogen peroxide generator.

2. The apparatus of claim 1, wherein the electrolyzer consumes a portion of the water from the water line to produce oxygen gas at the anode of the electrolyzer and hydrogen gas at the cathode of the electrolyzer, and wherein the anode of the electrolyzer is in fluid communication with the cathode of the electrochemical hydrogen peroxide generator and the cathode of the electrolyzer is in fluid communication with the anode of the electrochemical hydrogen peroxide generator.

3. The apparatus of claim 2, wherein the electrochemical hydrogen peroxide generator is a half fuel cell.

4. The apparatus of claim 2, wherein the electrolyzer comprises a single cell.

5. The apparatus of claim 2, wherein the electrolyzer comprises a proton exchange membrane electrolyzer.

6. The apparatus of claim 2, wherein the electrolyzer comprises a multi-cell stack.

7. The apparatus of claim 2, further comprising a DC power supply in electrical communication with the electrolyzer.

8. The apparatus of claim 7, further comprising a controller for monitoring and controlling the performance of the pasteurizer, hydrogen peroxide generator, electrolyzer, and the DC power supply.

9. The apparatus of claim 2, wherein the anode of the electrochemical hydrogen peroxide generator has an outlet in fluid communication with a catalyzed substrate, the catalyzed substrate having a structure and composition similar to an automotive catalytic converter.

10. The apparatus of claim 1, further comprising a filter immediately upstream of the fluid outlet.

11. The apparatus of claim 10, wherein the filter has a pore size of between 0.3 and 0.6 μm.

12. The apparatus of claim 11, wherein the pore size is about 0.45 μm.

13. The apparatus of claim 1, further comprising a first check valve at the water inlet to the water line and a second check valve immediately upstream of the fluid outlet.

14. The apparatus of claim 1, further comprising a holding tank for storing hydrogen peroxide, wherein the cathode of the electrochemical hydrogen peroxide generator is in fluid communication with the holding tank.

15. The apparatus of claim 14, wherein the holding tank has a fluid outlet in fluid communication with the water line downstream of the pasteurizer.

16. The apparatus of claim 1, wherein the electrochemical hydrogen peroxide generator has an anode inlet in fluid communication with the water line, and wherein the cathode inlet is in fluid communication with a source of oxygen.

17. The apparatus of claim 1, further comprising a heat exchanger providing thermal communication between the water line downstream of the pasteurizer and the water line upstream of the pasteurizer.

18. The apparatus of claim 1, wherein the water line extending between the inlet to the pasteurizer and the outlet from the pasteurizer provides a water residence time greater than one minute at the maximum water flow rate through the water line.

19. The apparatus of claim 18, wherein the maximum water flow rate is about 125 mL/min and the water line tubing has a diameter of at least 0.25 inches.

20. The apparatus of claim 1, further comprising a controller for controlling the delivery of hydrogen peroxide into the water line.

21. The apparatus of claim 20, wherein the controller provides a continuous delivery of hydrogen peroxide.

22. The apparatus of claim 20, wherein the controller provides a periodic delivery of hydrogen peroxide.

23. The apparatus of claim 20, wherein the controller provides hydrogen peroxide to the water line during periods of nonuse, wherein the hydrogen peroxide concentration in the water line is greater than two percent.

24. The apparatus of claim 1, wherein the pasteurizer is a thermally regenerative pasteurizer.

25. The apparatus of claim 24, wherein the thermally regenerative pasteurizer comprises a heat exchanger coupled with the pasteurizer.

26. The apparatus of claim 25, wherein the heat exchanger comprises a counter flow shell-in-tube design.

27. The apparatus of claim 26, further comprising a first thermocouple located at an exit from the tube side of the heat exchanger, a second thermocouple located inside a pasteurizer coil, and a third thermocouple located at an exit from the shell side of the heat exchanger.

28. The apparatus of claim 1, wherein the water flowing through the water line has a residence time of at least one minute in thermal communication with the heater of the pasteurizer.

29. The apparatus of claim 28, wherein the heater of the pasteurizer further comprises a thermal ballast to supply heat and damp out temperature swings during periods of intermittent water flow through the water line.

30. The apparatus of claim 29, wherein the thermal ballast is a preheated heat sink.

31. The apparatus of claim 28, wherein the heater of the pasteurizer heats the water flowing through the water line preferably to a temperature of at least 60° C.

32. The apparatus of claim 28, wherein the heater of the pasteurizer heats the water flowing through the water line more preferably to a temperature of at least 76° C.

33. The apparatus of claim 28, wherein the heater of the pasteurizer heats the water flowing through the water line preferably to a temperature of at least 90° C.

34. The apparatus of claim 1, wherein the electrochemical hydrogen peroxide generator comprises a single electrochemical cell.

35. The apparatus of claim 34, wherein the single electrochemical cell comprises an anode, a cathode, and a solid polymer electrolyte disposed between the anode and the cathode.

36. The apparatus of claim 34, wherein the single electrochemical cell comprises an anode compartment for receiving hydrogen gas and a cathode compartment for receiving oxygen gas.

37. The apparatus of claim 36, wherein both the oxygen and hydrogen gases are humidified.

38. The apparatus of claim 37, wherein the humidified oxygen and hydrogen gases are fed to the cathode and anode compartments, respectively, under pressure.

39. The apparatus of claim 38, wherein the pressure is at least 40 psi.

40. The apparatus of claim 1, wherein the electrochemical hydrogen peroxide generator comprises a multi-cell stack.

41. The apparatus of claim 1, wherein the cathode of the hydrogen peroxide generator produces an aqueous hydrogen peroxide solution.

42. The apparatus of claim 41, wherein the concentration of hydrogen peroxide is at least 0.1 wt %.

43. The apparatus of claim 41, wherein the concentration of hydrogen peroxide is at least 1.0 wt %.

44. The apparatus of claim 41, wherein the concentration of hydrogen peroxide is at least 3.0 wt %.

45. The apparatus of claim 1, further comprising a water prefilter and a deionization unit.

46. The apparatus of claim 45, wherein the water prefilter and the deionization unit are disposed in the water line between a first check valve and the pasteurizer.

47. The apparatus of claim 45, wherein the water prefilter has a pore size of 35 $\mu$m.

48. The apparatus of claim 1, wherein the water line is a dental water line.

49. The apparatus of claim 1, further comprising:
an injection port for adding one or more disinfectants, wherein the injection port is in fluid communication with the water line.

50. An apparatus for combating biofilms in a water line, comprising:
a pasteurizer receiving the water line, the pasteurizer having a heater capable of heating the water flowing through the line to a temperature greater than 65° C.;
an electrochemical hydrogen peroxide generator having a cathode in fluid communication with the water line downstream of the pasteurizer, wherein the cathode produces hydrogen peroxide;
a fluid outlet in fluid communication with the water line downstream of the hydrogen peroxide generator;
an electrolyzer having an anode in fluid communication with the water line, wherein the electrolyzer consumes a portion of the water from the water line to produce oxygen gas at the anode and hydrogen gas at the cathode, and wherein the oxygen gas is in fluid communication with the cathode of the electrochemical hydrogen peroxide generator and the hydrogen gas is in fluid communication with the anode of the electrochemical hydrogen peroxide generator; and
a filter immediately upstream of the fluid outlet.

51. The apparatus of claim 50, wherein the water line is a dental water line.

52. The apparatus of claim 50, further comprising:
an injection port for adding one or more disinfectants, wherein the injection port is in fluid communication with the water line.

53. A method for disinfecting water passing through a water delivery system, comprising:
pasteurizing the water as it passes through the water delivery system;
electrochemically consuming a portion of the water in an electrolyzer to produce hydrogen gas and oxygen gas;
electrochemically consuming at least a portion of the oxygen gas in an electrochemical hydrogen peroxide generator to produce hydrogen peroxide;
introducing the hydrogen peroxide into the water passing through the water delivery system; and
allowing the water to flow through the water delivery system on demand.

54. The method of claim 53, wherein the water is pasteurized by heating the water to a temperature greater than 65° C.

55. The method of claim 53, wherein the water is pasteurized by heating the water to a temperature greater than 90° C.

56. The method of claim 53, further comprising delivering an amount of hydrogen peroxide on demand to the water passing through the water delivery system.

57. The method of claim 53, further comprising delivering an amount of hydrogen peroxide continuously to the water passing through the water delivery system.

58. The method of claim 53, further comprising electrochemically consuming at least a portion of the hydrogen gas in the electrochemical hydrogen peroxide generator.

59. The method of claim 53, further comprising:
injecting one or more disinfectants into the water delivery system, wherein the disinfectants are injected through an injection port in fluid communication with the water delivery system.

60. A system for reducing water borne pathogens in a water pipeline, comprising:
a regenerative pasteurizer disposed in the pipeline; wherein the pasteurizer has a water inlet and a water outlet;
an electrochemical hydrogen peroxide generator, wherein hydrogen peroxide produced by the generator is introduced into the water pipeline upstream of the water outlet; and
an electrolyzer in fluid communication with the water pipeline downstream of the pasteurizer, wherein hydrogen gas and oxygen gas generated by the electrolyzer are communicated to the electrochemical hydrogen peroxide generator for the production of hydrogen peroxide, and wherein the system eliminates the need to maintain and periodically add stored chemical reagents.

61. The system of claim 60, wherein the water pipeline is a dental water pipeline.

62. A system for the prevention and remediation of biofilms in a water line, comprising:
a water pasteurizer comprising a heater and a heat exchanger disposed in the water line downstream of a water inlet;
an electrochemical hydrogen peroxide generator in fluid communication with the water line downstream of the pasteurizer; and
a fluid outlet in fluid communication with the water line downstream of the hydrogen peroxide generator, wherein the system requires only electricity and the water flowing in the water line to operate.

63. The system of claim 62, further comprising an electrolyzer having an anode in fluid communication with the water line downstream of the pasteurizer, wherein the electrolyzer consumes a portion of the water from the water line to produce oxygen gas at the anode of the electrolyzer and hydrogen gas at the cathode of the electrolyzer.

64. The system of claim 63, wherein the oxygen gas is communicated to a cathode of the hydrogen peroxide generator and the hydrogen gas is communicated to an anode of the hydrogen peroxide generator, and wherein at least some of the oxygen gas and at least some of the hydrogen gas are consumed electrochemically in the production of hydrogen peroxide.

65. The system of claim 64, wherein the electrolyzer comprises a multi-cell stack.

66. The system of claim 62, wherein the water flowing through the water line has a residence time of at least one minute in thermal communication with the heater of the pasteurizer.

67. The system of claim 62, wherein the heater of the pasteurizer heats the water flowing through the water line to a temperature of at least 60° C.

68. The system of claim 62, wherein the heater of the pasteurizer heats the water flowing through the water line more to a temperature of at least 76° C.

69. The system of claim 62, wherein the heater of the pasteurizer heats the water flowing through the water line to a temperature of at least 90° C.

70. A The system of claim 62, wherein the electrochemical hydrogen peroxide generator comprises a single electrochemical cell.

71. The system of claim 70, wherein the single electrochemical cell comprises an anode compartment for receiving hydrogen gas and a cathode compartment for receiving oxygen gas.

72. The system of claim 71, wherein both the oxygen and hydrogen gases are humidified.

73. The system of claim 72, wherein the humidified oxygen and hydrogen gases are fed to the cathode and anode compartments, respectively, under pressure.

74. The system of claim 73, wherein the pressure is at least 40 psi.

75. The system of claim 70, wherein the single electrochemical cell comprises an anode, a cathode, and a solid polymer electrolyte disposed between the anode and the cathode.

76. A The system of claim 75, wherein the cathode of the hydrogen peroxide generator produces an aqueous hydrogen peroxide solution.

77. The system of claim 76, wherein the concentration of hydrogen peroxide is at least 0.1 wt %.

78. The system of claim 76, wherein the concentration of hydrogen peroxide is at least 1.0 wt %.

79. The system of claim 76, wherein the concentration of hydrogen peroxide is at least 3.0 wt %.

80. The system of claim 63, wherein the electrolyzer comprises a single cell.

81. The system of claim 63, wherein the electrolyzer comprises a proton exchange membrane electrolyzer.

82. The system of claim 63, further comprising a DC power supply in electrical communication with the electrolyzer.

83. The system of claim 82, further comprising a controller for controlling the performance of the pasteurizer, hydrogen peroxide generator, electrolyzer, and the DC power supply.

84. The system of claim 63, wherein the anode of the electrochemical hydrogen peroxide generator has an outlet in fluid communication with a catalyzed substrate, the catalyzed substrate having a structure and composition similar to an automotive catalytic converter.

85. The system of claim 62, further comprising a water prefilter and a deionization unit.

86. The system of claim 85, wherein the water prefilter and the deionization unit are disposed in the water line between a first check valve and the pasteurizer.

87. The system of claim 85, wherein the water prefilter has a pore size of 35 $\mu$m.

88. The system of claim 62, wherein the electrochemical hydrogen peroxide generator comprises a multi-cell stack.

89. The system of claim 62, wherein the water line is a dental water line.

90. The system of claim 62, further comprising:
an injection port for adding one or more disinfectants, wherein the injection port is in fluid communication with the water line.

* * * * *